United States Patent [19]
Arciszewski et al.

[11] Patent Number: 4,565,089
[45] Date of Patent: Jan. 21, 1986

[54] CONSISTOMETER

[75] Inventors: Henry Arciszewski, Franklin Lakes; Linda A. Porzio, North Haledon, both of N.J.; Bin Y. Chiang, Little Neck, N.Y.

[73] Assignee: Nabisco Brands, Inc., Parsippany, N.J.

[21] Appl. No.: 621,961

[22] Filed: Jun. 18, 1984

[51] Int. Cl.$^4$ .............................................. G01N 3/48
[52] U.S. Cl. ........................................ 78/82; 73/169; 73/12; 73/85; 73/863
[58] Field of Search ...................... 73/82, 85, 169, 12, 73/87, 863, 78, 81, 83, 84, 79; 426/231

[56] References Cited

U.S. PATENT DOCUMENTS

| | | | |
|---|---|---|---|
| 1,458,130 | 6/1923 | Davis | 73/169 |
| 1,468,900 | 9/1923 | Chopin | 73/169 |
| 1,887,850 | 11/1932 | Bonney et al. | 73/85 |
| 2,030,475 | 2/1936 | Shore | 73/85 |
| 2,119,699 | 6/1938 | Bloom | 73/169 |
| 2,347,082 | 4/1944 | Claus | 73/169 |
| 2,567,333 | 9/1951 | Gogan | 73/81 X |
| 2,630,704 | 3/1953 | Armstrong | 73/12 |
| 2,975,631 | 3/1961 | Hansen | 73/169 |
| 3,123,998 | 3/1964 | Newman | 73/83 |
| 3,435,658 | 4/1969 | Arthur | 73/82 X |
| 3,482,430 | 12/1969 | Percorpio et al. | 73/79 X |
| 3,750,467 | 8/1973 | Rubro et al. | 73/169 |
| 3,899,931 | 8/1975 | Iwasaki | 73/78 X |
| 4,495,792 | 1/1985 | Bai et al. | 73/12 |

FOREIGN PATENT DOCUMENTS

| | | | |
|---|---|---|---|
| 820815 | 11/1951 | Fed. Rep. of Germany | 73/81 |
| 547387 | 12/1922 | France | 73/81 |
| 903602 | 10/1945 | France | 73/169 |
| 983828 | 6/1951 | France | 73/84 |
| 1206824 | 2/1960 | France | 73/169 |
| 58399 | 10/1967 | German Democratic Rep. | 73/81 |
| 255141 | 1/1949 | Switzerland | 73/82 |
| 506804 | 5/1976 | U.S.S.R. | 73/169 |
| 646223 | 2/1979 | U.S.S.R. | 73/169 |

Primary Examiner—Stewart J. Levy
Assistant Examiner—Tom Noland
Attorney, Agent, or Firm—Richard Kornutik

[57] ABSTRACT

An improved consistometer has a vertically-movable rod for imparting a precisely-measurable amount of energy on initial impact to a dough sample. Simultaneously, a precise measurement of vertical drop is obtained from a cooperating dial displacement indicator. The dial indicator has a vertical arm which is displaced by a horizontal disk fixed to the rod. A collar retains the rod in a first position; removal of the collar permits the rod to drop. After initial impact, further displacement of the rod is measured over a fixed time interval. Comparison of displacement of various dough samples thus indicates their relative consistencies. The rod has interchangeable penetrating rod end elements, to accommodate various types of dough.

26 Claims, 10 Drawing Figures

CONSISTOMETER

BACKGROUND OF THE INVENTION

This invention relates to consistometers for measuring the consistency of a dough sample, and particularly to a consistometer having an improved construction for precisely measuring vertical displacement of a rod into a dough sample. Also, this inventon relates to consistometers having interchangeable penetrating rod ends.

This invention may also be adapted for use as a consistometer for measuring any of a variety of edible food products, including but not limited to breads, pastries, fillings, cookies, crackers, laminated food products, or any other edible goods which have a measurable consistency.

In the conventional consistometers, a weight is released against a dough or food sample. The dough or food sample is respectively penetrated to broken. The prior art testers commonly use gauges to measure displacement, the gauge usually being directly connected to a testing arm which moves into the dough or food sample. Such consistometers do not have conveniently interchangeable penetrating rod ends. Moreover, such prior art consistometers do not have a readily variable weight attached to the vertically displaced penetrating rod end which could be used to adapt the consistometer for varying doughs or varying materials to be tested. Also, since the prior art consistometers that rely on a dial indicator for precise measurements have included it with the dropping rod assembly, the weight of the rod cannot be measured independently of the dial indicator. This is undesirable, in that a consistometer ideally should be usable with any of a variety of food products or doughs, and in order to provide the most significant measurements the weight of a falling mass used to penetrate the dough or food product sample must be variable, and should be susceptible of precise measurement without complete disassembly of the consistometer. Furthermore, the rod should be separately removable from the consistometer without disturbing the dial indicator so that the rod assembly may be periodically cleaned and inspected without contacting the dial indicator. Such contact or bumping of the dial indicator in a disassembly operation might ordinarily damage it or cause a previous calibration to become inaccurate. Also, dial indicators are easily suspectible to being broken or otherwise damaged by impacts such as might occur if the dial indicator were removed from its support stand.

Other prior art devices, which do not use dial indicators, have simpler operation and structure but are not as precise as those devices using a dial indicator. In such devices, marks have been placed along one moving part and the gross movement is detectable by relative movement of the marks against a second, fixed part. While being convenient to use, these devices suffer from a lack of accuracy. Furthermore, in these devices, objective measurements are very difficult to obtain since the point of view of the observer and the acuity of the observer's vision are influencing factors in the measurement which is ultimately recorded by the observer.

The prior art consistometers employ release mechanisms of varying types. However, the prior art release mechanisms either reply upon complex linkages or else are clumsy and awkward to use with one hand if an observer if using the other hand to operate a stopwatch or timer. Thus, ease of operation is an important quality in a consistometer, as is reliability and accuracy.

Attempts have been made in the prior art to overcome the disadvantages associated with the prior art consistometers. Typical of the prior art attempts to solve the above-noted problems associated with consistometers is the type disclosed by Claus in U.S. Pat. No. 2,347,082 and Bloom in U.S. Pat. No. 2,119,699. Other inventors have made varying attempts to solve the above-identified problems, and those effects are also discussed below.

U.S. Pat. No. 1,458,130 discloses a process and apparatus for classifying food products, wherein a C-shaped support portion having a forked upper arm slidably retains a cylinder having a variable weight (a shot-bearing cup) attached to the top. The weight is supported upon a horizontal disk. The slidable cylinder has interchangeable striking members attached to the bottom thereof, a striking member being retained in place by a setscrew. A baking sample is elevated slightly above the lower portion of the C-shaped support member by a pair of rails which are parallel to, but offset from, the elongated striking member. In testing the samples, the total weight of the rod assembly (including the upper shot-bearing cup and the lower striking member) is measured, and the rod assembly is allowed to fall a predetermined distance so as to break the baked good sample. If, however, the baked good sample does not break, more weight is added to the shot-bearing cup and the process is repeated. However, no dial indicator is used for measuring displacement, nor are rod-shaped, alternate plungers used as striking members. Furthermore, the upper disk portion of the vertically traveling rod is not used to measure vertical travel.

The U.S. Pat. No. 2,119,699 discloses a consistency tester having a dial pressure indicator attached to the uppermost end of a cylinder, the lower end of the cylinder having a slidable piston mounted therein which is attached at its lowermost extremity to a special head used to penetrate a food product sample. Glycerin is retained in the otherwise hollow portion of the upper end of the cylinder so as to transmit force from the movable rod to the pressure gauge. The special heads are interchangeable, and the vertically movable rod has a shoulder thereon for limiting downward travel through the hollow cylinder. In operation, the consistency tester is pushed into a dough sample until the special head has completely penetrated the dough sample. From this point on a constant pressure reading will be obtained, and this reading may be compared with other dough samples. However, a C-shaped support stand is not shown not is a horizontal disk used to displace an instrument arm to provide a measure of vertical displacement of a rod. Furthermore, no dial indicator for indicating vertical travel is shown.

The U.S. Pat. No. 2,347,082 discloses a method and apparatus for testing dough, having a vertically adjustable dial indicator mounted to an upstanding support rod which is attached fixedly to a bottom table support. A rounded dough contacting element is vertically centered beneath the dial indicator. Three vertically adjustable support arms are also attached to the rod between the dial indicator support arm and the lower table portion, the uppermost and the lowermost arms used to constrain the vertical movment of a rod which passes through openings in each of the arms. The rod is attached at is uppermost portion to the dial indicator and at its lowermost portion to the dough contacting head.

A third arm between the two constraining arms has a hanged joint therein. The extremity of the jointed arm contacts a vertically hanging, adjustable support arm which can be pivoted out of supporting engagement of the extremity. The pivoting support arm contacts a pin fixed to the vertically movable rod so that disengagement of the support arm permits the rod to fall downward from an accurately predetermined distance. The dial indicator measures vertical displacement of the rod. Upon release of the load on the dough specimen, a stopwatch is started to that the amount of compression can be read at definite time intervals and recorded to indicate any variation in the time compression reading. In a second embodiment a counterweight is used to accurately balance the weight of the specimen engaging member so that only a selected amount of weight is applied to the dough sample regardless of the position of the testing apparatus. However, a C-shaped support member having a dial vertical travel indicator at an upper extremity thereof with a vertical travel indicating rod adapted to contact at an upper end of the dial a portion of a vertically movable rod is not shown. Further, interchangeable dough contacting elements are not shown, nor is a setscrew shown to engage the rod to limit vertical downward travel of the rod to limit vertical downward travel.

The U.S. Pat. No. 2,975,631 shows a softness gauge for bakery products wherein a hollow, cylindircal support element receives a rod member with a weight attached to its top, and a dough contacting element at its bottom. A portion of the rod within the cylinder is exposed so that a calibration mark is visible thereon, and corresponding marks are present on the portion of the cylinder closely adjacent the exposed portion of the rod so that relative travel of the rod and cylinder may be readily measured. In use, a dough sample is placed directly under the rod, the weight released, and vertical travel downwards measured. However, no dial indicator for indicating vertical relative movement is shown, no C-shaped support is shown having a dial indicator attached to its upper extremity for contacting an upper portion of a vertically movable rod which has a setscrew for adjusting a predetermined distance of fall for the rod. Further, no interchangeable dough contacting elements are shown.

The U.S. Pat. No. 3,750,467 discloses a device to measure compressibility of soft materials. Here, an overall C-shaped stand has three rods. A middle rod has calibrating indicia thereon and has at its top a support ring for attaching to the uppermost extremity of the top support. On either side are two rods which are constrained to move along a vertically fixed axis. The rods are fixedly attached at their lower extremities to a dough contacting element. In use, the ring is disconnected from the uppermost support member, and vertical travel in a downward direction of the assembly against a dough sample is measured by observation of the relative displacement of the indicia upon the indicia bearing rod relative to a fixed plate. However, no dial indicator is shown for measuring vertical displacement of a fixed rod member. Further, no interchangeable dough contacting elements are shown, nor is a dial indicator shown which is attached to an extremity of an upper C-shaped support member.

The French patent No. 903,602 shows a fixed support plaform for a movable rod. The rod has a calibrating mark thereon and is placed centrally within apertures in support member. A vertical scale is placed closely adjacent to the calibrating mark. In use, the support member is placed upon a dough sample and the weight is released. Vertical downward travel of the weight into the dough sample is then recorded by comparing the relative beginning and ending levels of the rod. However, no C-shaped support member is shown having a vertical travel indicating dial indicator thereon at an upper extremity thereof, nor is there shown a rod mounted for vertical travel within the upper C-shaped member such that its upper portion bears a horizontal surface for contact with an operatively attached rod of the dial indicator for indicating relative movement therebetween. Further, no interchangeable dough contacting elements are shown.

The French patent No. 1,206,824 shows a more complex device for indicating travel of a rod within a support member. However, no C-shaped support member is shown which supports a dial indicator to an upper arm, nor is contact shown of a rod with a horizontal surface of a vertically movable member. Further, no interchangeable dough contacting elements are shown.

Russian patent No. 506,804 discloses a complex consistency measuring device for use with soft food products. An indenter is motor-driven into a tested sample and a dynamometer measures the consistency while a potentiometer measures the electrical resistance so as to indicate food quality. However, no C-shaped support member is shown for supporting at its upper arms's extremity a dial indicator having a rod operatively attached thereto for contacting a horizontal upper surface of a vertically movable member for contacting a dough sample. Further, no interchangeable dough contacting elements are shown.

SUMMARY OF THE INVENTION

It is accordingly one object of the present invention to provide an improved consistometer which is reliable, accurate, requires no extraordinary equipment in the fabrication thereof, and that is formed of readily available materials that can be manufactured by persons skilled in the mechanical arts.

Another object of the present invention is to provide an improved consistometer having a vertically dropping rod with a penetrating rod end, and which together are supported by a C-shaped stand.

A further object of the present invention is to provide an improved consistometer which can be operated by one hand when necessary, including a pull chain for removal of a predetermined-width spacing member.

A still further object of the present invention is to provide an improved consistometer which includes a C-shaped support stand, a vertically dropping rod, interchangeable penetrating rod ends, a dial indicator which is not directly connected to the vertically dropping rod, and a horizontal disk atop the vertically dropping rod which actuates an arm of the dial indicator.

A still further object of the present invention is to provide an improved consistometer for measuring consistency of a dough sample of predetermined thickness, including an associated device having two spaced bars between which a dough sample is placed, and having a rolling pin and a cookie sheet, so that a plurality of uniform dough samples may be produced and tested, and the results of the measurements may be compared.

Another object of the present invention is to provide an improved consistometer having a C-shaped support stand, a horizontally disposed middle guide bar for stabilizing and guiding a penetrating rod end of a vertically movable rod, a manually removable spacer and support element for initiating falling of the rod, a dial indicator having an arm in contact with a horizontal disk attached to the rod so that falling of the rod is indicated by the dial indicator.

A still further object of the present invention is to provide an improved consistometer having a C-shaped support stand, a vertically displaceable rod having interchangeable penetrator rod ends, a spacer member for precisely positioning the vertically displaceable rod which can be manually removed by a pulling action, and a dough sample of a predetermined thickness which is prepared by being rolled by a rolling pin between two flat spacer bars upon a conventional cookie sheet, so that a plurality of dough samples taken from a plurality of batches may all be rolled to a uniform thickness and then measured under the penetrating rod ends of the consistometer.

The improved consistometer of the present invention comprises a C-shaped support stand having a dial indicator mounted at the upper end of the stand adjacent the furthest edge of the C-shape. A vertical bore is formed in the uppermost arm of the C-shaped stand, and is adapted to permit sliding passage of a cylindrical rod therethrough.

A lower portion of the rod has a tap drilled therein for receiving a threaded fastener member of alternate penetrating rod ends so that varying diameters of rod ends may be used. A horizontal cylindrical disk having a bore therethrough is fixed at a location near the upper end of the rod. The horizontal disk is adapted to contact and displace a vertical arm of the dial indicator so that displacement of the vertical arm of the dial indicator may be measured.

Intermediate the top of the C-shaped support stand and the horizontal disk fixed to the rod is a detachable collar. The collar is formed in the shape of a generally semi-cylindrical sleeve having one side substantially removed so that from a top view the detachable collar itself appears to comprise a C-shape. A chain is attached both to the detachable collar and to the C-shaped support stand so that upon sudden force exerted against the chain the detachable collar will be jerked free and the horizontal disk will no longer be supported. Thus, the weight of the rod and the horizontal disk causes the rod and disk assembly to fall against a dough sample.

The dough sample is placed upon the lower end of the C-shaped support stand directly beneath the penetrating rod end. Upon release of the rod assembly, the penetrating rod end falls against the dough sample, and the impact causes immediate deformation of the dough sample. A timer monitors the passage of time, while the dial indicator monitors the precise distance traveled into the dough by the penetrating rod end. Penetration of the rod assembly into the dough sample is monitored over a period of time until a specified penetration or a specified time has elapsed. No full penetration of the dough sample is made. Thus, the softness of various dough may be directly measured. For example, various batches of dough having different chemical compositions may be measured for softness and a consistent measure of softness obtained in all cases. Furthermore, the effect of time upon various dough samples is also measurable, since allowing dough to stand for a long period of time will generally toughen the dough and make it less soft. In this way, consistency of a plurality of different samples of dough can be measured.

The horizontal disk member may be readily attached to the rod or detached from it by means of a pair of setscrews which are screwed through a collar fixedly attached to the horizontal disk member. Thus, the assembly may be readily disassembled or adjusted for drop height. For example, for a thick dough a greater drop height is desirable. In this case, the setscrews would be loosened and the horizontal disk assembly moved downward relative to the rod. When the detachable collar is inserted between the upper arm of the C-shaped support stand and the lower end of the horizontal disk assembly, the lower penetrating rod end is raised to a greater height above the bottom arm of the C-shaped support stand thereby allowing a thicker dough sample to be inserted beneath it.

Further details and advantages of the present invention appear from the following description of a preferred embodiment shown schematically in the drawings.

DETAILED DESCRIPTION OF THE INVENTION

Figure 1:
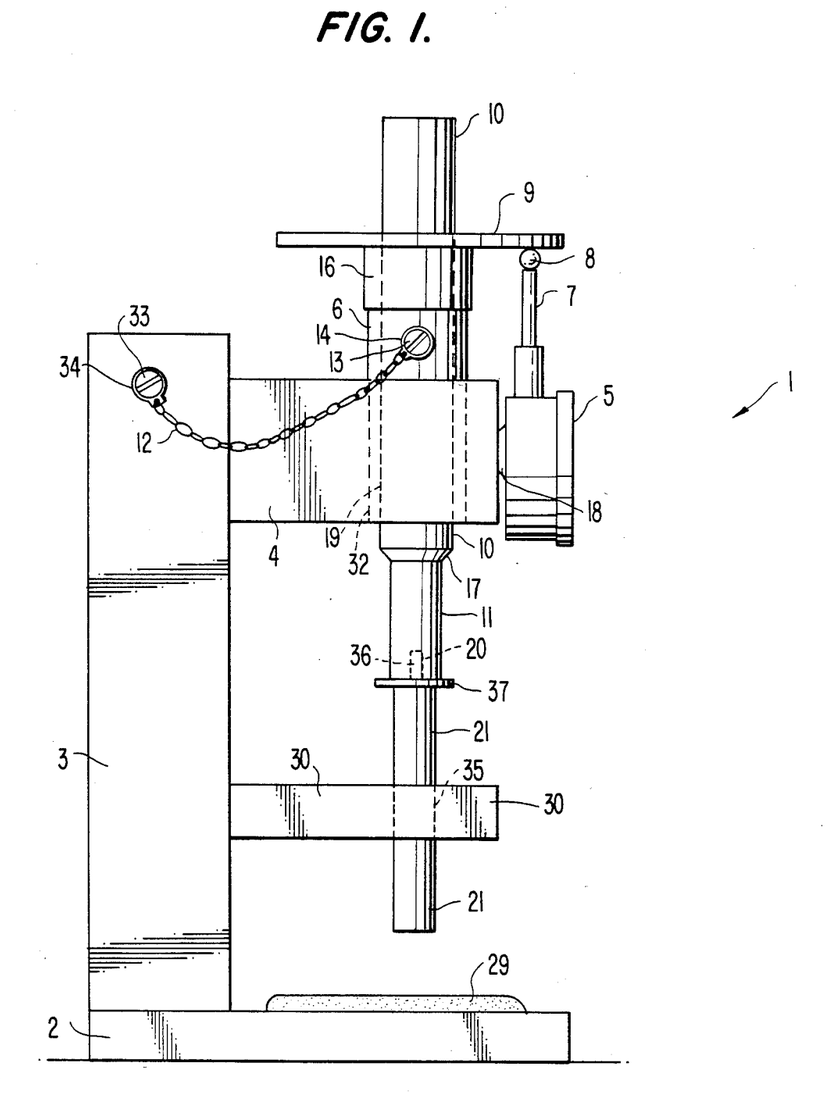
FIG. 1 shows a side elevational view of a consistometer of the present invention.

A consistometer is shown in a side plan view in FIG. 1. As can be seen, the consistometer 1 is composed of a plate which serves as base 2 of the stand, a vertical support post 3 which is fixedly attached to the base plate 2, and a horizontal support arm 4 which is fixedly attached at a top portion of vertical support post 3. The attachments may be made by any known means, for example welding, use of threaded fasteners, epoxy glue, and the like.

A dial indicator 5 having a vertical arm 7 is attached to horizontal support arm 4 by connecting arm 18. The vertical arm 7 is movable relative to the dial indicator 5 such that vertical displacement of the vertical arm 7 relative to the dial indicator 5 is indicated on the face of the dial indicator 5 by a pointer. The dial indicator 5 indicates displacements accurately to as little as one one-thousandth of an inch. The dial indicator may be any known dial displacement indicator, and in a preferred embodiment a Teclock ® brand indicator is used. The vertical arm 7 of the dial displacement indicator 5 has an enlarged vertical arm tip 8 for contacting another part of the apparatus which is movable so as to displace the vertical arm 7. The dial indicator 5 includes gearing, which is conventional, as that a relatively small displacement of the arm 7 results in a relatively large dial displacement.

The horizontal support arm 4 has a bore 19 formed therein generally near the end of horizontal support arm 4 that is furthermost from vertical support post 3. The bore 19 may be formed by simply drilling through and boring the material of horizontal support arm 4, or in a preferred embodiment the bore 19 is formed by the inner surface of a bushing 32 which is in a preferred embodiment formed of bronze. The bushing 32 itself would be fixed in place in a bore formed in horizontal support arm 4 in the preferred embodiment. The bore 19 is adapted to permit sliding passage of a rod 10 therethrough.

The rod 10 is cylindrical and is sized so as to fit snugly within bore 19 without significant frictional resistance to sliding movement of rod 10 therethrough.

A horizontal disk 9 is fixedly attached to a sleeve 16. The sleeve 16 has a pair of bores formed therein adapted to receive setscrews 15 therein. The horizontal disk 9 and the sleeve 16 both have a passage therethrough adapted to receive rod 10. As shown in FIG. 1, the horizontal disk 9, which is fixedly attached to sleeve 16, is mounted upon rod 10 such that rod 10 passes through the hole formed in horizontal disk 9 and sleeve 16. In a preferred embodiment, the hole formed in horizontal disk 9 and sleeve 16 is a cylindrical bore which is coaxial with both the disk 9 and sleeve 16. Also in the preferred embodiment, the bore passing through disk 9 and sleeve 16 snugly receives rod 10. Setscrews 15 (shown in FIG. 2) are screwed into sleeve 16 such that they pass through the thickness of a well of sleeve 16 and abut rod 10. Further tightening of setscrews 15 results in very strong frictional contact of setscrews 15 with the rod 10, thereby retaining the disk 9 and its associated sleeve 16 firmly against rod 10.

Figure 3:
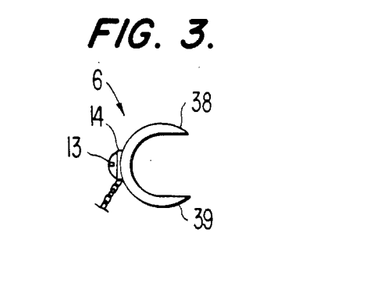
FIG. 3 shows a top elevational view of the detachable collar used in the consistometer of the present invention.
Figure 4A:
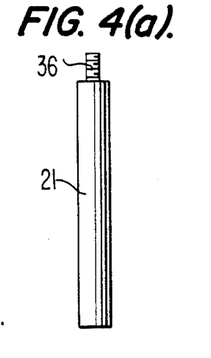
FIGS. 4a, 4b, 4c, and 4d show alternate penetrating rod ends usable with the consistometer of the present invention.
Figure 4B:
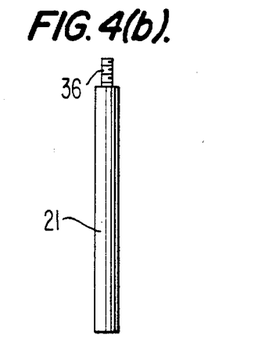
Figure 4C:
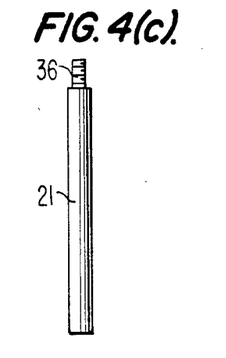
Figure 4D:
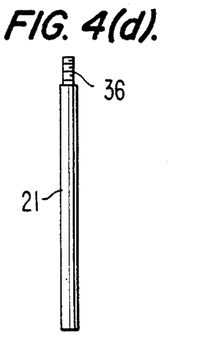

Rod 10 is mounted in bore 19, as shown in FIG. 1, while the horizontal disk 9 and fixedly attached sleeve 16 are spaced above horizontal support arm 4 by detachable collar 6. The detachable collar 6 has a diameter greater than that of bore 19, and is open along one side as shown in FIG. 3. The sleeve 16 has a slightly larger diameter than that of detachable collar 6, and is adapted to rest thereon. The contact surfaces between detachable collar 6 and support arm 4 are sufficiently smooth that no significant resistance is encountered against sliding motion of the detachable collar 6 relative to horizontal support arm 4. Also, the contact surfaces between sleeve 16 and detachable collar 6 are sufficiently smooth that no significant frictional resistance is encountered between sliding of detachable collar 6 against sleeve 16. A chain 12 is attached to the detachable collar 6 by a screw 13. The chain 12 is in turn fixedly attached to vertical support post 3 by a screw 33 which passes through a fastener washer 34 which is fixedly attached to chain 12. A similar fastener or washer 14 is used with screw 13 to attach the chain to detachable collar 6. The chain 12 is sufficiently strong that it may be jerked or yanked manually in a sudden motion with one hand so as to slide detachable collar 6 suddenly away from horizontal support arm 4 and sleeve 16 so as to allow rod 10 to drop.

The rod 10 is sufficiently long that it passes entirely through bore 19 and below the lower surface of horizontal support arm 4. The rod 10 tapers to a somewhat smaller diameter as indicated by taper 17, at a location below the lower surface of horizontal support arm 4. A middle guide plate 30 extends generally parallel to horizontal support arm 4 and is spaced therefrom along vertical support post 3. The middle guide plate 30 is fixedly attached to the vertical support post 3. A bore 35 is formed in middle guide plate 30 and is adapted to snugly receive a penetrating rod end 21 in sliding contact therewith.

The penetrating rod end 21 is attached fixedly to the lowermost end of tapered rod end 11 by a threaded protrusion 36 which is integral with penetrating rod end 21. The lowermost portion of rod 10 is designated as tapped rod end 11. A tapped hole 20 is formed in tapped rod end 11. The tapped hole 20 has a generally cylindrical form and and has its cylindrical axis oriented parallel with that of rod 10, and in a preferred embodiment the cylindrical axis of tapped hole 20 is co-linear with the central cylindrical axis of rod 10. Thus, penetrating rod end 21 is screwed into tapped hole 20 so as to become fixedly attached to rod 10 at tapped rod 11. Middle guide plate 30 prevents wobbling during operation of penetrating rod end 21 due to clearance which may exist in bore 19, since some clearance, however small, must exist in order to prevent strong frictional contact between bore 19 and rod 10.

The attachments between vertical support post 3 and base plate 2, as well as between horizontal support arm 4 and vertical support post 3, and between middle guide plate 30 and vertical support post 3, are made by any known attaching means, including welding, epoxy glue, threaded fastener members, and the like. Nonetheless, many variations of construction may be used, for example the entire support stand including base plate 2, vertical support post 3, horizontal support arm 4, and middle guide plate 30 may be formed from a single cast piece of material. The material may include, but is not limited to, steel, plastic, bronze, iron, copper, ceramic material, or any other known material having sufficient strength to support the weight or rod 10 and avoid breakage of base plate 2 during deformation of a dough sample 29.

Figure 2:
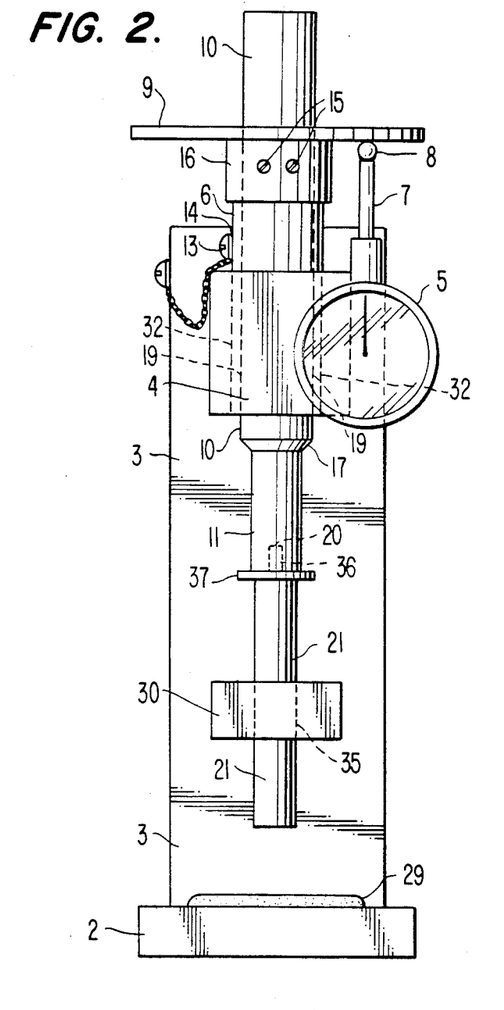
FIG. 2 shows a front elevational view of the consistometer of the present invention.

In FIG. 2 is shown a front elevational view of the consistometer of the present invention. As can be seen, the dial indicator 5 is mounted to the right-hand side of horizontal support arm 4 and is therefore somewhat off-center of a plane of vertical symmetry of the support stand. In the preferred embodiment, bore 19 and bore 35 are centered along the vertical plane of symmetry of the support stand. Nonetheless, the bores 19,35 may be located with their centers in a common vertical plane that is not coincidental with the vertical plane of symmetry of the support stand, without departing from the present invention. Furthermore, although rectangular prismatic solid elements are shown for the elements of the support stand, especially base plate 2, vertical support post 3, horizontal support arm 4, and middle guide plate 30, any solid shape may be used for any of the above-mentioned elements without departing from the scope of the present invention. Nonetheless, rectangular prismatic solids were chosen as the preferred embodiment of the present invention due to ease of assembly, ease of machining where required, and the convenience and cost savings inherent in using plate and bar shapes which are conventional and which are readily available commercially.

A flange 37 may be formed at the lowermost edge of tapered rod end 11. However, the flange 37 is not necessary to the present invention and may be omitted if desired, although such is not the preferred embodiment.

The dough sample 29 is shown in FIGS. 1 and 2 as lying flat and coplanar with the top surface of base plate 2. The dough sample 29 is placed upon base plate 2 such that a portion of the dough sample 29 lies directly beneath penetrating rod end 21.

Detachable collar 6 is shown in FIG. 3 in a top elevational view. As can be seen, the detachable collar 6 is generally cylindrical and has a cylindrical passage therethrough. A side of the detachable collar 6 is removed such that the inner diameter of the opening in detachable collar 6 is equal to the size of the rod 10. Thus, removal of the detachable collar 6 from rod 10 will not be impeded by inward curvature of two ends 38,39 of the generally C-shaped detachable collar 6. The location of screw 13 and fastener washer 14 is also shown in FIG. 3.

Alternate sizes of penetrating rod ends 21 are shown in FIGS. 4a, 4b, 4c, and 4d. As can be seen, threaded portions 36 all are the same size in each of these figures, however diameter of the penetrating rod end portions 21 vary. For example, a main penetrating rod end 21 may have a diameter of ⅝ inch; alternate penetrating rod ends 21 may have respective diameters of ½ inch, 7/16 inch, ⅜ inch, and ¼ inch. The threading on treaded protrusion 36 in each of the respective figures may be any desired threading. The length of each protusion may typically be 7/16 inch. The length of penetrating rod ends 21 exclusive of threaded protrusion 36 may typically be 4-3/16 inches. The overall height of the consistometer of the present invention may be about 1 foot and the length of base plate 2 may be in the range of about 7 inches. It is contemplated that the widths of base plate 2, vertical support post 3, and horizontal support arm 4, be of the order of 2-3 inches. However, it is within the scope of the present invention that any relative dimensions be used, without departing from the scope of the present invention.

Figure 5:
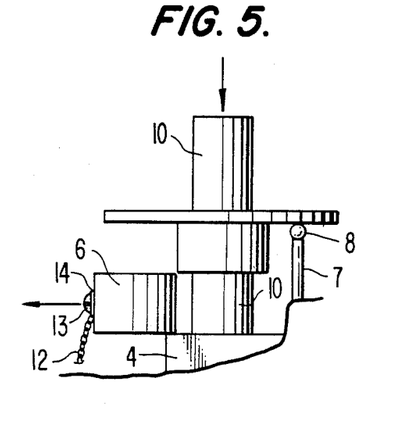
FIG. 5 is a front elevational view of the consistometer of the present invention as the detachable collar is being inserted.

FIG. 5 shows the relative position of detachable collar 6 to rod 10. In this position, the rod 10 is held in position while the detachable collar 6 is slid into place beneath it. The weight of rod 10 is then released against detachable collar 6 so that the weight of rod 10 rests upon the detachable collar 6.

Figure 6:
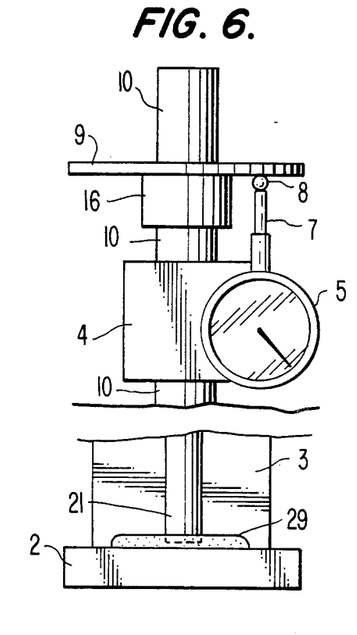
FIG. 6 is a front elevational view of the top portion of the consistometer of the present invention after the detachable collar has been removed.

The relative positions of rod 10 and horizontal support arm 4 are shown in FIG. 6 after removal of detachable collar 6. In this figure, rod 10 has descended to a point where it is still above the top surface of horizontal support arm 4 but further movement is significantly retarded by dough sample 29 beneath penetrating rod end 21. The middle portion of the consistometer 1 is broken away in FIG. 6 so that only the top portion of horizontal support arm 4, and the bottom portion of penetrating rod end 21 and dough sample 29 are shown.

Figure 7:
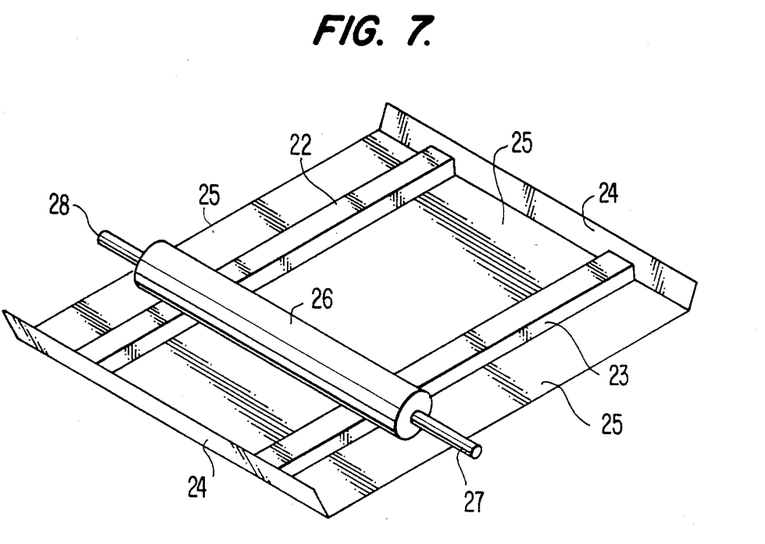
FIG. 7 is a perspective view of the apparatus used in preparing dough samples for testing in the consistometer of the present invention.

A cookie sheet 24 is shown in FIG. 7. Prismatic rectangular bars 22,23 are spaced in parallel relationship across the interior portion 25 of the cookie sheet 24. A dough sample would be rolled between prismatic rectangular bars 22,23 by a rolling pin 26 having handles 27,28. The thickness of each of rectangular prismatic bars 22,23 determines the thickness to which a dough sample 29 can be rolled. In a preferred embodiment, the cookie sheet 24 is formed of aluminum and may optionally have a Teflon ® coating if desired. Nonetheless, any material for the cookie sheet 24 may be used, and any shape of cookie sheet 24 may be used. The rectangular prismatic bars 22,23 may also be of any material, including wood, iron, steel, plastic, or the like, so long as they are strong enough to withstand breaking or substantial deformation during the rolling operation by roller 26.

In operation, the consistometer of the present invention is placed on any flat horizontal surface as desired. A dough sample 29 is rolled between rectangular prismatic bars 22,23 on the cookie sheet 24. A rolller 26 rolls the dough sample 29 flat. The flat dough sample 29 is then transported, usually immediately, to the top of base plate 2 where it is rested. A central portion of dough sample 29 rests directly beneath penetrating rod end 21 of rod 10.

An operator may then ready a stopwatch or other timer, not shown, in operation for the subsequent test. At the start of the test, the timer is actuated simultaneously with the sudden removal of detachable collar 6. Rod 10 falls until penetrating end 21 impacts against the dough sample 29. The dial indicator 5 is then read and the measurement noted of the distance vertical arm 7 has traveled downward. After a substantial amount of time has elapsed, for example five minutes to fifteen minutes, a second reading is then taken of the dial indicator 5 to show further deformation of the dough sample 29. The initial dial indicator 5 reading following initial impact of the penetrating rod end 21 against the dough sample 29 may then be subtracted from the final reading at the end of the predetermined period of time to obtain the distance traveled by the penetrating rod end 21 into the dough sample 29. This would yield a significant measure of the softness of the dough sample 29.

The particular diameter of the penetrating rod end 21 is selectable as suggested in FIGS. 4a–4d. This prevents excessive penetration of the dough sample 29 in the case of an especially soft dough, inasmuch as the penetration of rod end 21 is approximately inversely related to the diameter of penetrating rod end 21. Therefore, if excessive penetration occurs during a test of a dough sample, the penetrating rod end 21 is replaced with a larger diameter penetrating rod end 21. Thus, the pressure applied per unit area of the dough sample 29 is diminished and penetration correspondingly reduced.

Excessive penetration of the penetrating rod end 21 into the dough sample 29 is to be avoided in that false readings occur when penetrating rod end 21 penetrates too closely to base plate 2. That is, the hardness of base plate 2 would actually become a part of the measurement of the softness of the dough sample 29 were excessive penetration to occur.

Although a cylindrical rod 10 is shown, and cylindrical bores 19,35 are shown, rod 10 could have any arbitrary cross-sectional shape provided bores 19 and 35 also had corresponding cross-sectional shapes. For example, a star-shaped rod may be used, or a rectangular one. Furthermore, although cylindrical penetrating rod ends 21 are shown, any cross-sectional shape may be used for the penetrating rod ends 21, for example the rod end 21 may be star-shaped, square, rectangular, rhomboidal, crescent-shaped, ellipsoidal, and the like may be used. Also, although a threaded protrusion 36 is shown cooperating with a tapped hole 20, any detachable fastening means may be employed to connect rod end 11 with penetrating rod end 21, such as a snap fastening, a horizontally oriented dovetail joint, clamp arms, an outer sleeve enclosing both rod end 11 and penetrating rod end 21, and the like. Furthermore, rod end 11 and penetrating rod end 21 may be selectively permanently attached as by welding, epoxy glue, or the like, although this is not the preferred embodiment. Furthermore, although a dough sample 29 is to be tested, any article which is deformable may be so tested, including pie filling, cookie dough, any type of putty, cement, mortar, plaster, jelly, or the like may be used. Also, although a particular pair of bars 22,23 and a particular cookie sheet 24 is used to provide uniformly thick dough samples, any method of providing uniformly thick dough samples may be used including a pair of spaced rollers, pressing between two flat surfaces, extruding, or the like, without departing from the scope of the present invention.

Although a horizontal disk 9 is shown for displacing vertical arm 7 to indicate displacement, any shape may be used for the disk 9, e.g., a single arm may be used fastened to the rod 10. Also, a square, ellipsoidal, or even a pretzel shaped member could be used instead of disk 9. The only requirements are that the member replacing the disk 9 be sufficiently rigid so as to displace arm 7 to the extent rod 10 drops, that the member replacing the disk 9 have a suitable weight, and that the member replacing the disk 9 be fixed to rod 10 for movement therewith.

The improved consistometer of the present invention is capable of achieving the above-enumerated advantages and objects and while preferred embodiments of the present invention have been disclosed, it will be understood that it is not limited thereto but may be otherwise embodied within the scope of the following claims.

We claim:

1. A consistometer for measuring the consistency of a deformable sample, comprising:
   a support having a means for guiding;
   a movable mass adapted to be guided in a downward direction under the force of gravity by said means for guiding;
   a means for indicating displacement having a displaceable arm contacting a portion of said movable mass;
   and a removable spacer element to suppot said movable mass in a predetermned spaced relation to said support, said removable spacer element being selectively disengageable from said support so as to release said movable mass;
   whereby disengagement of said removable spacer element from said support causes said movable mass to drop vertically under the force of gravity against a deformable specimen placed thereunder, so that said means for indicating can indicate depth of penetration into the deformable specimen by said movable mass;
   said support including a vertical post supporting a horizontal arm in spaced relation from a base, whereby the specimen can rest upon said base beneath said movable mass for testing;
   said means for guiding including an aperture formed in said horizontal arm which extends completely therethrough, said movable mass being adapted to be received within said aperture, whereby said movable mass remains substantially vertically oriented during testing;
   said movable mass including a rod having a diameter adapted to be received within said aperture;
   said rod having a means for contacting a portion of said displaceable arm attached thereto;
   whereby downward movement of said movable mass causes said means for contacting to urge said displaceable arm of said means for indicating displacement such that displacement of said movable mass is indicated by said means for indicating displacement;
   said means for contacting including generally horizontally extending body which is attached to a portion of said rod;
   said horizontally extending body being attached to said rod at a location above said horizontal arm;
   said movable mass comprising an elongated article;
   said removable spacer element has an indentation therein adapted to abut said elongated article;
   said removable spacer element having a lower surface adapted to slidably rest upon an upper surface of said horizontal arm;
   said removable spacer element having an upper surface adapted to slidably support a horizontally extending portion of said movable mass;
   whereby said removable spacer element stably supports said movable mass in spaced relation to said horizontal arm.

2. A consistometer as claimed in claim 1 above, wherein said movable mass comprises a selectively interchageable penetrating rod end, whereby particular penetrating rod end may be selected for the particular specimen to be tested without disassembly of other portions of the support or the movable mass.

3. A consistometer as claimed in claim 1 above, wherein said horizontally extending body further comprises a lower portion having at least one threaded bore therethrough for receiving a setscrew so that the horizontally extending body is attachable at any selected position on the rod, whereby samples of varying thickness can be accommodated.

4. A consistometer as claimed in claim 3 wherein said elongated article has along at least a portion of its length a uniform cross-section;
   said aperture having a cross-section which is slightly larger than the cross-section of said portion of said elongated article that has the uniform cross-section;
   said aperture being adapted to slidably receive the portion of said elongated article having said uniform cross-section;
   whereby said aperture guides said elongated article in a substantially straight line.

5. A consistometer as claimed in claim 4 above, wherein said movable mass comprises an end which is adaped to receive a penetrating rod end.

6. A consistometer as claimed in claim 5 above, wherein said end has a tapped hole therein;
   said penetrating rod end having a threaded projection adapted to be received in said tapped hole;
   whereby the selected penetraing rod end is detachably fixed to said end.

7. A consistometer as claimed in claim 5, above, wherein said end and said penetrating rod end are connected together by a means for attaching;
   whereby the selected penetrating rod end is detachably fixed to said end.

8. A consistometer as claimed in claim 5 above, wherein a plurality of penetrating rod ends are provided;
   each penetrated rod end having a predetermined cross-sectional area and length;
   whereby a penetrating rod end may be selected so that a selected cross-sectional area and length is available for use with the particular sample.

9. A consistometer as claimed in claim 4 above, wherein said sample comprises dough for use in edible food products.

10. A consistometer as claimed in claim 4 above, wherein a second horizontal arm is fixed to said post;
said second horizontal arm having an aperture extending therethrough which is located in alignment with said aperture formed in said horizontal arm;
whereby said second horizontal arm provides additional guidance for said movable mass.

11. A consistometer as claimed in claim 4 above, wherein said means for indicating displacement further comprises a dial indicator which is indicative of displacement of said arm contacting a portion of said movable mass;
whereby an accurate determination of displacement of said movable mass can be quantified.

12. A consistometer as claimed in claim 4 above, wherein said means for indicating further comprises a means for gearing so that a relatively small displacement of said arm results in a relatively large movement of said dial.

13. A consistometer as claimed in claim 4 above, wherein said uniform cross-section of said portion of said elongated article therewith is circular;
said cross-section of said aperture being circular and slightly larger than the cross-section of said portion of said elongated article that is of uniform cross-section.

14. A consistometer as claimed in claim 4 above, wherein said cross-section of said portion of said elongated article that is of uniform cross-section is non-circular;
said cross-section of said aperture having a substantially similar non-circular cross-section which is slightly larger than the cross-section of said portion of said elongated article that is of uniform cross-section.

15. A consistometer as claimed in claim 4 above, wherein said horizontal arm comprises a prismatic solid having a rectangular cross-section in any vertical plane therethrough which does not intersect the aperture.

16. A consistometer as claimed in claim 4 above, wherein said support is metal.

17. A consistometer as claimed in claim 4 above, wherein said movable mass is metal.

18. A consistometer as claimed in claim 4 above, wherein said support is formed of plastic.

19. A consistometer as claimed in claim 4, in combination with a device for rolling samples to a uniform thickness;
said device further comprising a pair of substantially identical bars having generally parallel upper and lower surfaces;
a sheet for support said bars; and
a rolling pin;
whereby a sample placed between said spacer bars may be rolled by the pin so that the thickness of the bars determines the thickness of the sample after it is rolled.

20. A device as claimed in claim 19 above, wherein said sheet is Teflon-coated and said sample is a dough sample.

21. A consistometer is claimed in claim 20 above, further comprising a means for timing which is adapted to be manually actuated;
whereby an observer may record the time at which a displacement reading taken, so that a measure of consistency over varying of periods of time may be determined.

22. A consistometer as claimed in claim 1, wherein said spacer element has a semi-cylindrical outer surface;
said spacer element has a semi-cylindrical inner surface coaxial with said outer surface;
said removable spacer element being adapted to support said movable mass in spaced relation to said horizontal arm in a stable position.

23. A consistometer as claimed in claim 22 above, wherein said cross-section of said portion of said elongated article that is of uniform cross-section is circular;
said inner surface of said removable spacer element being defined by a radius that is slightly larger than the radius of the circle defined by said cross-section of said portion of said elongated article that is of uniform cross-section;
whereby said removable spacer snugly receives said portion of said elongated article that is of uniform cross-section.

24. A consisitometer for measuring the consistency of a deformable sample, comprising:
a support having a means for guiding;
a movable mass adapted to be guided in a downward direction under the force of gravity by said means for guiding;
a means for indicating displacement having a displaceable arm contacting a portion of said movable mass;
and a removable spacer element to support said movable mass in a predetermined spaced relation to said support, said removable spacer element being selectively disengagable from said support so as to release said movable mass;
whereby disengagement of said removable spacer element from said support causes said movable mass to drop vertically under the force of gravity against a deformable specimen placed thereunder, so that said means for indicating can indicate depth of penetration into the deformable specimen by said movable mass;
said support including a vertical post supporting a horizontal arm in spaced-relation from a base, whereby the specimen can rest upon said base beneath said movable mass for testing;
said means for guiding including an aperture formed in said horizontal arm which extends completely therethrough, said movable mass being adapted to be received within said aperture, whereby said movable mass remains substantially vertically oriented during testing;
said movable mass including a rod having a diameter adapted to be received within said aperture;
said rod having a means for contacting a portion of said displaceable arm attached thereto;
whereby downward movement of said movable mass causes said means for contacting to urge said displaceable arm of said means for indicating displacement such that displacement of said movable mass is indicated by said means for indicating displacement;
said means for contacting including a generally horizontally extending body which is attached to a portion of said rod;
said horizontally extending body being attached to said rod at a location above said horizontal arm;
said horizontally extending body further comprising a lower portion having at least one threaded bore therethrough for receiving a setscrew so that the horizontally extending body is attachable at any selected position on the rod, whereby samples of varying thickness can be accommodated;

said movable mass comprising an elongated article having along at least a portion of its length a uniform cross-section;

said aperture having a cross-section which is slightly larger than the cross-section of said portion of said elongated article that has the uniform cross-section;

said aperture being adapted to slidably receive the portion of said elongated article having said uniform cross-section;

whereby said aperture guides said elongated article in a substantially straight line;

said removable spacer element having an indentation therein adapted to abut said elongated article;

said removable spacer element having a lower surface adapted to slidably rest upon an upper surface of said horizontal arm;

said removable spacer element having an upper surface adapted to slidably support a horizontally extending portion of said movable mass;

whereby said removable spacer element stably supports said movable mass in spaced relation to said horizontal arm.

25. A consistometer as claimed in claim 24, wherein said spacer element has a semi-cylindrical outer surface;

said spacer element has a semi-cylindrical inner surface coaxial with said outer surface;

said removable spacer element being adapted to support said movable mass in spaced relation to said horizontal arm in a stable position.

26. A consistometer as claimed in claim 25 above, wherein said cross-section of said portion of said elongated article that is of uniform cross-section is circular;

said inner surface of said removable spacer element being defined by a radius that is slightly larger than the radius of the circle defined by said cross-section of said portion of said elongated article that is of uniform cross-section;

whereby said removable spacer snugly receives said portion of said elongated article that is of uniform cross-section.

* * * * *